US005611084A

United States Patent [19]
Garry et al.

[11] Patent Number: 5,611,084
[45] Date of Patent: Mar. 18, 1997

[54] JACKET WITH INTEGRAL BACK SUPPORT

[75] Inventors: Jeffrey R. Garry, Sioux Falls, S. Dak.; Gary Luskey, Fort Worth, Tex.

[73] Assignee: Raven Industries, Inc., Sioux Falls, S. Dak.

[21] Appl. No.: 496,859

[22] Filed: Jun. 30, 1995

Related U.S. Application Data

[63] Continuation of Ser. No. 203,264, Feb. 28, 1994, abandoned.

[51] Int. Cl.⁶ ..................................................... A41D 1/00
[52] U.S. Cl. ............................... 2/93; 2/108; 2/102; 2/44
[58] Field of Search ............................. 2/44, 92, 93, 85, 2/95, 108, 311, 338, 322, 2, 69, 94, 227; 602/19, 20; 128/78, 874, 100.1, 101.1, 121.1, 96.1

[56] References Cited

U.S. PATENT DOCUMENTS

| | | |
|---|---|---|
| 4,175,553 | 11/1979 | Rosenberg . |
| 4,302,847 | 12/1981 | Mills . |
| 4,813,080 | 3/1989 | Toso . |
| 4,833,730 | 5/1989 | Nelson . |
| 5,007,412 | 4/1991 | DeWall . |
| 5,086,759 | 2/1992 | Buddingh . |
| 5,105,474 | 4/1992 | Skinner ........................................ 2/69 |
| 5,157,790 | 10/1992 | Aldridge ..................................... 2/227 |
| 5,179,942 | 1/1993 | Drulias et al. . |
| 5,241,704 | 9/1993 | Sydor . |
| 5,257,419 | 11/1993 | Alexander .................................... 2/44 |
| 5,274,851 | 1/1994 | Simpkins, Sr. et al. ...................... 2/44 |
| 5,351,340 | 10/1994 | Aldridge ..................................... 2/108 |

FOREIGN PATENT DOCUMENTS

| | | | |
|---|---|---|---|
| 2501974 | 9/1982 | France ........................................ 2/108 |
| 2259848 | 3/1993 | United Kingdom ....................... 2/338 |

Primary Examiner—C. D. Crowder
Assistant Examiner—Gloria Hale
Attorney, Agent, or Firm—Hill, Steadman & Simpson

[57] ABSTRACT

An outer garment such as a vest having an integral back supporting belt having a pair of inner straps for closing the belt around the wearer and outer tightening straps for pulling a lumbar supporting region tight to the wearer's back.

10 Claims, 3 Drawing Sheets

JACKET WITH INTEGRAL BACK SUPPORT

This is a continuation of application Ser. No. 08/203,264, filed Feb. 28, 1994 now abandoned.

BACKGROUND OF THE INVENTION

The present invention relates to an integral garment and back support, particularly to a jacket or vest with an integral cummerbund-style back support.

Many occupations and recreational activities require the participant to wear an outer garment for warmth such as a vest or jacket. Additionally, the same activities can require long periods of sitting or strenuous activity which can cause back fatigue and soreness. In many outdoor activities, an individual must be seated upright on a flat surface without a rigid back support, such as on the ground or floor, or in a backless chair, bench, saddle or the like. These positions can be uncomfortable because of the lack of support at the lumbar region and such discomfort will often occur after a relatively short period of time for persons with poor posture and/or weak back structures.

U.S. Pat. Nos. 5,086,759; 5,179,942; 4,175,553; and 4,833,730 all disclose back supporting belts having, in some cases, inner and outer belt portions using hook and loop fasteners for attachment. U.S. Pat. No. 5,007,412 and U.S. Pat. No. 5,241,704 disclose work aprons having integral back supports.

U.S. Pat. No. 4,813,080 describes a complex back supporting device included with an upper torso garment, wherein the back support is tightened by a wearer's knees when the wearer is sitting.

It is not known from these references to provide an outer garment having an integral or attached wrap around, cummerbund-style, back supporting belt.

SUMMARY OF THE INVENTION

It is an object of the present invention to provide a lumbar supporting, wrap-around belt formed integrally with or attached to an outer garment. It is an object of the invention to provide an effective construction for fixing the supporting belt at a particular orientation with respect to the wearer such that the belt can be quickly and accurately fastened in position with respect to the lumbar region of the wearer.

It is an object of the present invention to provide a jacket and back supporting belt which can be quickly put on and which can be easily tightened or loosened without removing the jacket or outer garment. It is an object of the present invention to provide an outer garment with an integral back supporting belt wherein the back supporting belt is not visible outside of the outer garment when the outer garment is closed or buttoned up. It is an object of the present invention to provide an outer garment and back supporting belt arrangement wherein the back supporting belt is permanently fastened to the outer garment to prevent separation when the jacket is removed by the wearer for storage. It is an object of the present invention to provide an outer garment and back supporting belt which is light weight and which has a common inner lining surface which makes for a comfortable fit and a smooth and orderly appearance to an inside of the garment.

The objects are inventively achieved in that an outer garment integral back supporting belt is provided which has an outer thermal layer and an inner lining surface including a lumbar support surface, the liner having side apertures for a portion of the back supporting belt to emerge in order to encircle the waist region of the wearer partly between the liner and the outer thermal layer. The back supporting belt has tightening straps which, in the lumbar region of the wearer, reside between the outer thermal layer and the lining. The lining is extended and adjustably fixed onto the strap portions which extend adjacent the side apertures.

The belt thus is configured with the strap portions encircling the waist of the wearer and the tightening straps encircling the strap portions and lumbar region and fixable in a stretched condition to the strap portions. The strap portions are fixed to each other using surface fastener coupling (hooks and loops) and the tightening straps are fixed to the strap portions also using a surface fastener coupling.

The outer garment can be a jacket or vest, can be a hunting jacket of an appropriate orange or neon color, or can be any number of outer garments which provide climatic protection for the wearer.

DETAILED DESCRIPTION OF THE PREFERRED EMBODIMENTS

Figure 1:
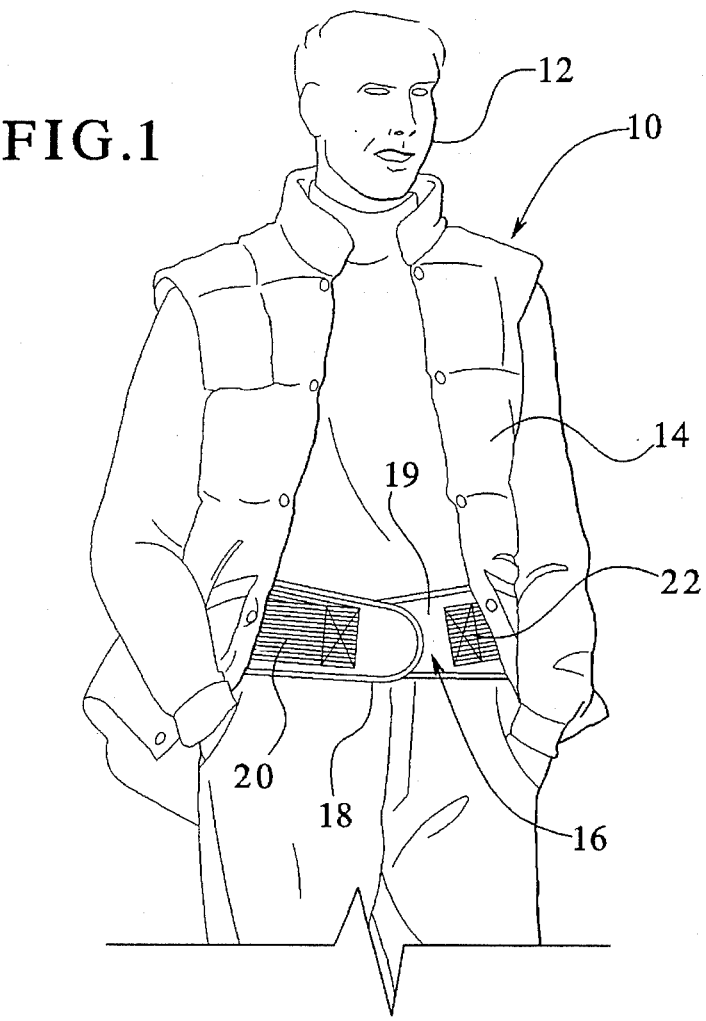
FIG. 1 is a perspective view of the garment of the present invention on a wearer.
Figure 3:
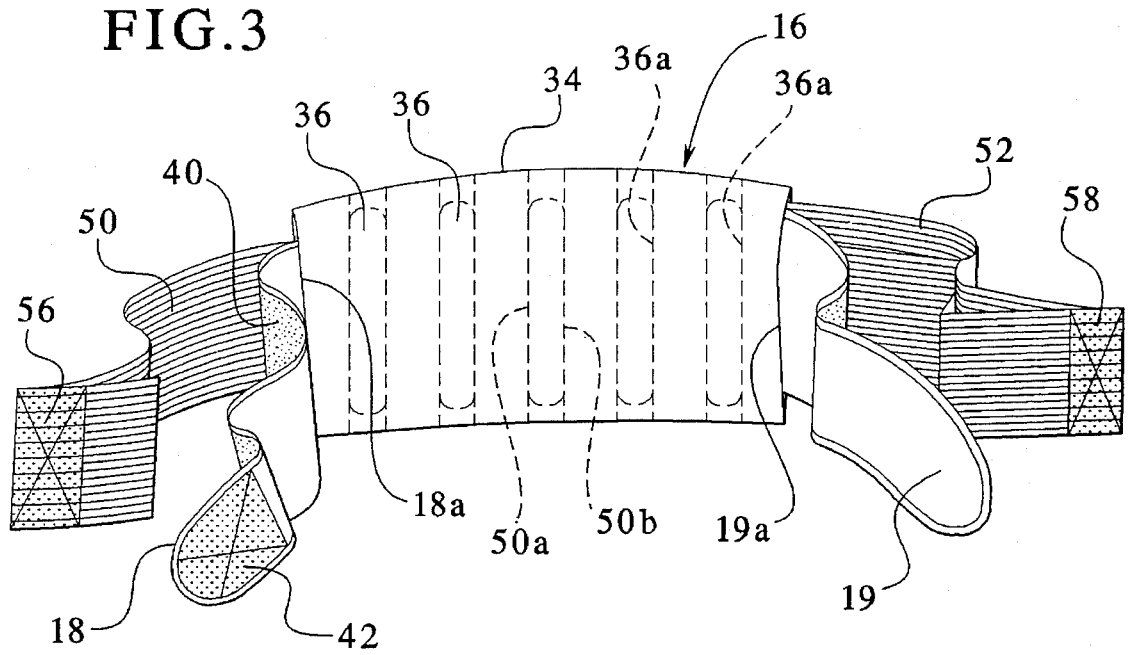
FIG. 3 is a perspective view of a portion of the garment shown in FIG. 2.
Figure 2:
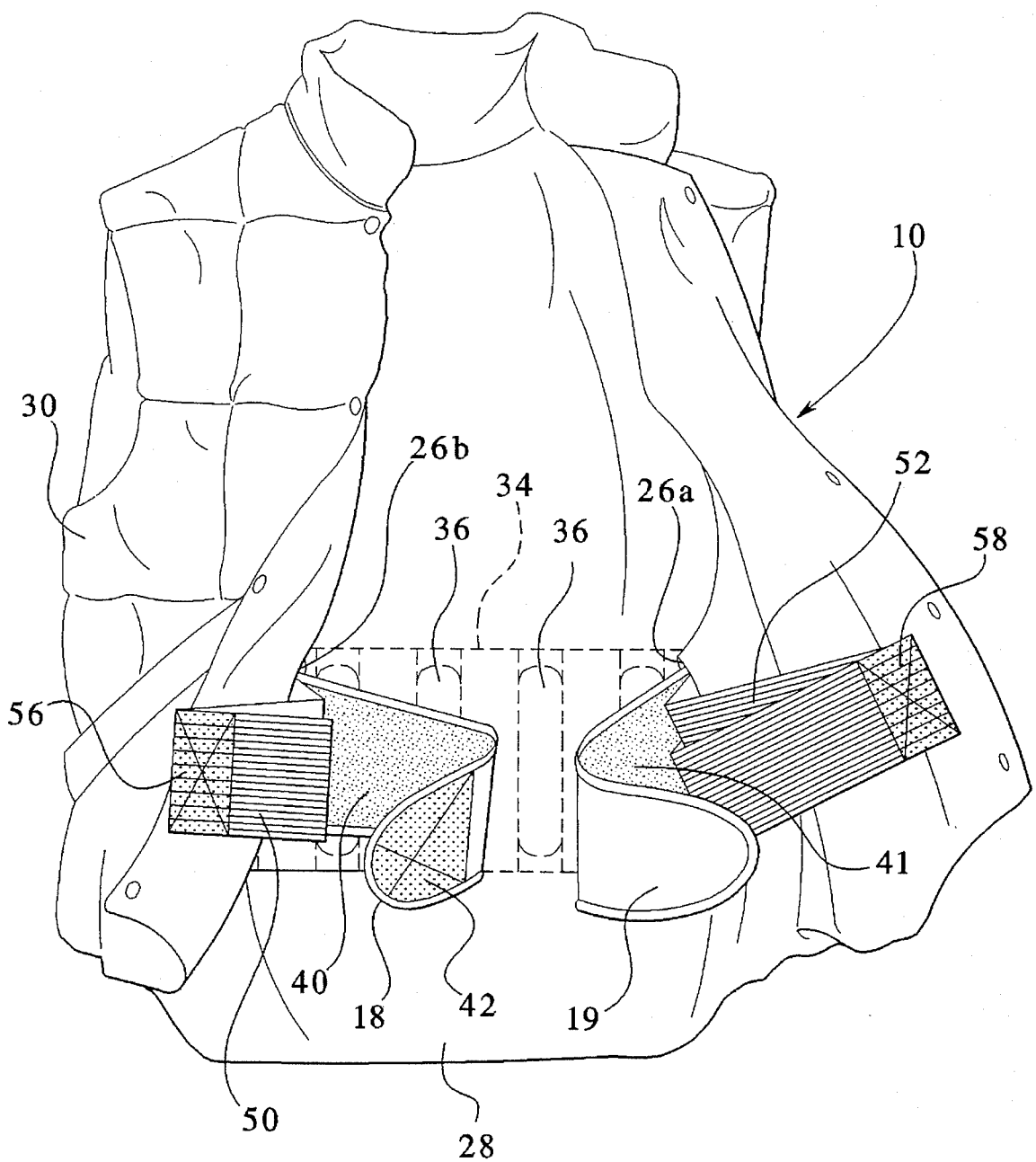
FIG. 2 is a perspective view of the garment of FIG. 1.

FIGS. 1–3 illustrate a garment 10 of the present invention on a wearer 12, the garment 10 includes cover garment 14 and an integral belt 16. The belt 16 provides a pair of inner straps 18, 19 and outer elastic tightening straps 20, 22 as will be described below.

FIG. 2 shows the garment such as a vest 10 in an open condition. The inner straps 18, 19 extends from a position adjacent to side apertures 26a, 26b through an inside lining 28 of the vest 10. The vest 10 also comprises a thermal outside layer 30 overlying the lining 28. The belt comprises a lumbar supporting region 34 shown dashed in FIG. 2. This region can be located between the lining 28 and the outside layer 30 or can be formed as part of the lining 28. The lumbar region 34 has a plurality of supporting elements 36. The elements 36 can be plastic resilient plates or "tongues" interfit into pockets 36a formed in the lumbar supporting region 34. When the lumbar region is formed integral with the liner, the pockets 36a can be attached to a backside of the liner.

The inner straps 18, 19 provide on a front facing surface first regions 40, 41 having a plurality of loops such as is known in hook and loop fastener designs (surface fasteners). On an inner surface of at least one end of the inner straps 18 is applied a region of engaging hooks 42 which can be engaged to the region 41 to connect free ends of the inner straps 18, 19 in a belt arrangement encircling the wearer. Arranged extending from the lumbar supporting region 34 parallel to the inner straps 18, 19 are two tightening straps 50, 52 each which can comprise a double layer elastic material. Each tightening strap 50, 52 has arranged thereon on an inwardly facing surface a region of hook elements 56, 58 respectively. Thus, when the inner straps 18, 19 are secured in an encircling position around the wearer, the tightening straps 50, 52 can be elastically stretched and fastened with the hook regions 56, 58 engaged to the respective surfaces 40, 41 to tighten the belt 16 around the wearer.

The tightening straps 50, 52 thread through the apertures 26a, 26b and are fastened to the lumbar region 34 of the belt.

Because the inner straps 18, 19 are secured at seams 18a, 19a at the lumbar supporting region 34, and the lumbar supporting region 34 can be integral with the lining or otherwise attached to the jacket, the belt 16 is rotationally oriented to the wearer merely by putting on the vest. The tightening straps 50, 52 are secured to the lumbar supporting region 34 at seams 50a, 50b.

Figure 4:
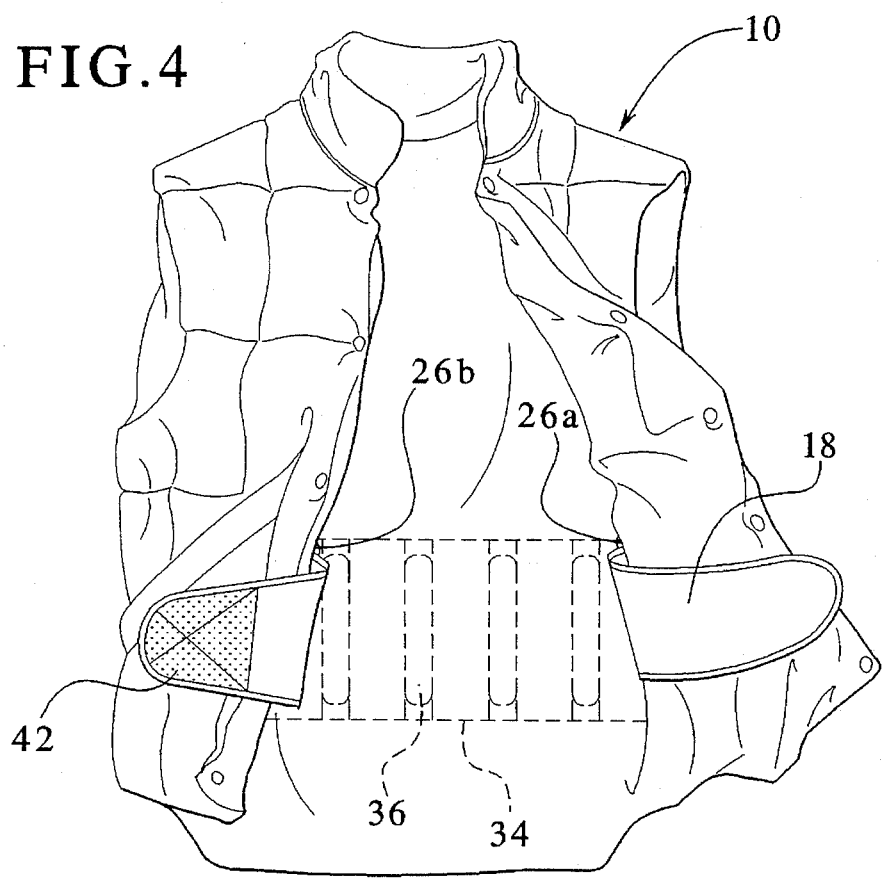
FIG. 4 is a perspective view of the garment of FIG. 2 showing an alternate mode of operation.

FIG. 4 shows the vest 10 in an open position wherein the tightening straps 50, 52 are secured to the inner straps 18, 19 and the jacket can be put on or removed by releasing only the region 42 from the region 41 of the inner strap 19. Thus, the tightening straps 50, 52 can remain at their adjusted stretched position and the wearer can put the vest 10 back on and secure the inner strap 18 to the inner strap 19.

Figure 5:
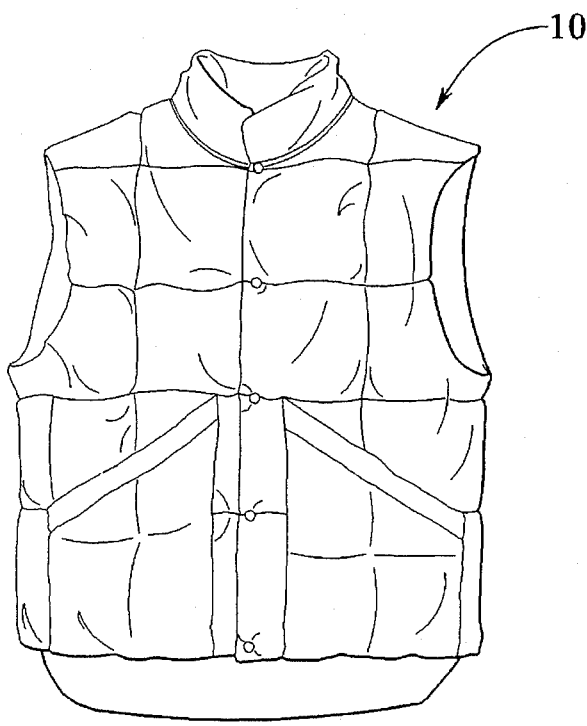
FIG. 5 is a perspective view of the garment of FIG. 2 shown closed or buttoned-up.

FIG. 5 shows the jacket in the closed condition and demonstrates that the belt is concealed completely by the vest 10.

Although the present invention has been described with reference to a specific embodiment, those of skill in the art will recognize that changes may be made thereto without departing from the scope and spirit of the invention as set forth in the appended claims. For example, the outer garment 10 may have sleeves and form a jacket. The fashioning of back supporting belt 16 can vary such as the various back supporting belts of the cited prior art. The regions of the belt specified as hooks or as loops of a surface fastener region can be, of course, interchanged.

I claim as my invention:

1. A garment for a person comprising:

an outer garment layer surrounding a substantial portion of a person's upper torso and having a closeable front seam; and an encircling back supporting belt having a substantial width for 360° around the torso for abdominal support connected to said outer garment layer, said back supporting belt having means for providing bending rigidity in a direction along the person's spine, said means including spaced apart flexible plate members, said belt having tightening straps engageable at a front side of the person's upper torso and completely concealed by said outer garment layer upon closure of said front seam; and said belt having an overlapping front region engageable by respective mating surface fastener regions applied between overlapping ends of the belt, and said belt end straps being independently closed with respect to said front seam of said outer garment layer such that said front seam of said outer garment layer can remain open with the overlapping front region of the belt being engaged.

2. A garment for a person comprising:

an outer garment layer surrounding a substantial portion of a person's upper torso; and an encircling back supporting belt connected to said outer garment layer, said back supporting belt having means for providing bending rigidity in a direction along the person's spine; and wherein said garment comprises a lining inside said outer garment layer, and said means for providing bending rigidity is located in a lumbar supporting region formed flush with, and fixed by sewing to, said lining, said lining, and said belt having two strap portions having a substantial abdominal supporting width extending therefrom to encircle the person and connect together, said strap portions extending from said lining and concealed by said outer garment layer when said front seam is closed; and said strap portions having an overlapping front region engageable by respective mating surface fastener regions applied between overlapping ends thereof, and said strap portions being independently engageable with respect to said front seam of said outer garment layer such that said front seam of said outer garment layer can remain open with the overlapping front region of the strap portions being engaged.

3. The garment according to claim 2, wherein said back supporting belt comprises elastic tightening straps extending from said lumbar supporting region around an outside of said strap portions, and said belt comprises fastening means for fixing distal ends of said tightening straps at positions on said strap portions.

4. The garment according to claim 3, wherein said means for providing bending rigidity comprises spaced apart vertical pockets and flexible plate members interfit into said pockets.

5. The garment according to claim 1, wherein said outer garment layer comprises a vest-shaped covering and fastening means for closing a front seam of said vest.

6. A garment for a person comprising:

an outer garment layer surrounding a substantial portion of a person's torso and having a closeable front seam secured by fasteners;

an encircling back supporting belt connected to said outer garment layer;

wherein said garment comprises a lining inside said outer garment layer, and said back supporting belt comprises a lumbar supporting region formed flush with said lining and having two strap portions extending therefrom having a substantial abdominal supporting width to encircle the person and connect together on a front side of the person's torso;

wherein said back supporting belt comprises elastic tightening straps extending from said lumbar supporting region around an outside of said strap portions, and said belt comprises fastening means for fixing distal ends of said tightening straps at positions on said strap portions; and wherein said tightening straps extend between said lining and said outer garment layer and are fastened to said lumbar supporting region at a central portion thereof, said outer garment layer concealing said back supporting belt when said front seam is closed; and said strap portions having an overlapping front region engageable by respective mating surface fastener regions applied between overlapping ends thereof, and said strap portions being independently engageable with respect to said front seam of said outer garment layer such that said front seam of said outer garment layer can remain open with the overlapping front region of the strap portions being engaged.

7. The garment according to claim 6, wherein said tightening straps comprise a dual layer elastic material.

8. A garment for a person comprising:

an outer garment layer surrounding a substantial portion of a person's torso;

an encircling back supporting belt connected to said outer garment layer;

wherein said back supporting belt comprises:

strap portions for encircling a wearer between said strap portions and a back side of said outer garment layer, said strap portions having a substantial abdominal supporting width completely around the wearer, said strap portions having first surface fastener regions on an outside surface thereof and one of said strap portions having a compatible second engaging surface fastener regions applied on an inner surface thereof for engagement with the respective other of said first surface fastener regions; and tightening straps fixed to said outer garment layer and stretchable around an outside of said strap portions and comprising compatible third surface fastener regions on an inner surface of distal ends thereof for fixing an elongation of said straps with respect to said portions by engagement of said third surface fastener regions to said first surface fastener regions; and wherein said outer garment layer completely conceals said encircling back supporting belt; and said strap portions and said tightening straps being independently engageable with respect to said front seam of said outer garment layer such that said front seam can remain open with the belt being completely engaged.

9. The garment according to claim 1, wherein said outer garment layer is configured as a jacket having sleeves.

10. A garment for a person comprising:

an outer garment layer surrounding a substantial portion of a person's upper torso, having a closeable front seam and a lining inside said outer garment layer;

an encircling back supporting belt connected to said outer garment layer, said back supporting belt having a lumbar supporting region including spaced apart vertical pockets and means for providing bending rigidity in a direction along the person's spine comprising flexible plate members which interfit into said pockets, said lumbar supporting region being flush with and fixed by sewing to said lining;

said back supporting belt having only one strap portion extending away from each lateral side of said lumbar supporting region, said strap portions having a length sufficient to encircle the person and connect together on a front side of the person's torso and having a substantial abdominal supporting width along their length;

both of said strap portions having a first surface fastener region provided on an outside surface thereof and one of said strap portions having a compatible second engaging surface fastener region applied on an inner surface thereof for engagement with said first surface fastener region on the other of said two strap portions;

said back supporting belt having only a single, dual layer, elastic tightening strap extending from each lateral side of said lumbar supporting region around an outside of a respective strap portion, with a third surface fastening region applied on an inner surface of a distal end of each of said elastic tightening straps for engagement with said first surface fastener region on said respective strap portion, said tightening straps extending between said lining and said outer garment layer and being fastened to said lumbar supporting region;

wherein said outer garment layer conceals said back supporting belt when said front seam is closed.

* * * * *

UNITED STATES PATENT AND TRADEMARK OFFICE
CERTIFICATE OF CORRECTION

PATENT NO. : 5,611,084
DATED : March 18, 1997
INVENTOR(S) : Garry et al.

It is certified that error appears in the above-indentified patent and that said Letters Patent is hereby corrected as shown below:

Column 5, line 37 (Claim 10, line 3),
reads as "person's" and it should read as "person'"

Claim 10, Line 2 "person'"

Signed and Sealed this

Fourteenth Day of July, 1998

Attest:

BRUCE LEHMAN

*Attesting Officer*    *Commissioner of Patents and Trademarks*